United States Patent
Göbelt et al.

(10) Patent No.: US 8,097,076 B2
(45) Date of Patent: Jan. 17, 2012

(54) WETTING AND DISPERSING AGENT

(75) Inventors: Bernd Göbelt, Wesel (DE); Carsten Nagel, Dülmen (DE); Jürgen Omeis, Dorstenlembeck (DE); Marcus Meichsner, Kamp-Lintfort (DE); Diana Walter, Valen (DE)

(73) Assignee: BYK-Chemie GmbH, Wesel (DE)

( * ) Notice: Subject to any disclaimer, the term of this patent is extended or adjusted under 35 U.S.C. 154(b) by 28 days.

(21) Appl. No.: 12/845,402

(22) Filed: Jul. 28, 2010

(65) Prior Publication Data
US 2010/0322879 A1 Dec. 23, 2010

Related U.S. Application Data

(63) Continuation of application No. PCT/EP2009/000699, filed on Feb. 3, 2009.

(30) Foreign Application Priority Data
Feb. 4, 2008 (DE) .......... 10 2008 007 713

(51) Int. Cl.
C09D 11/00 (2006.01)

(52) U.S. Cl. ........... 106/31.86; 106/31.28; 106/31.89; 347/100; 516/204; 524/366; 524/376; 524/505; 524/513; 524/559; 525/166; 525/172; 525/173; 525/176; 525/404; 525/408; 525/438; 525/445

(58) Field of Classification Search ........ 106/31.28, 106/31.86, 31.89; 347/100; 516/204; 524/366, 524/376, 505, 513, 559, 824; 525/166, 172, 525/173, 176, 404, 408, 438, 445
See application file for complete search history.

(56) References Cited

U.S. PATENT DOCUMENTS

| | | | |
|---|---|---|---|
| 4,243,430 A | 1/1981 | Sperry et al. | |
| 4,647,647 A | 3/1987 | Haubennestel et al. | |
| 5,085,698 A | 2/1992 | Ma et al. | |
| 5,160,372 A | 11/1992 | Matrick | |
| 5,519,085 A | 5/1996 | Ma et al. | |
| 6,242,499 B1 | 6/2001 | Grunning et al. | |
| 6,291,620 B1 | 9/2001 | Moad et al. | |
| 6,683,121 B2 | 1/2004 | Chiou et al. | |
| 6,849,679 B2 | 2/2005 | Auschra et al. | |
| 2004/0143035 A1 | 7/2004 | Goebelt et al. | |
| 2006/0008942 A1 | 1/2006 | Romano et al. | |
| 2006/0069224 A1 | 3/2006 | Pritchins et al. | |
| 2007/0018527 A1 | 1/2007 | Neet | |
| 2009/0095202 A1 * | 4/2009 | Fechner et al. | 106/31.86 |

FOREIGN PATENT DOCUMENTS

| | | |
|---|---|---|
| EP | 1 54 678 A1 | 9/1985 |
| EP | 0 270 216 A2 | 6/1988 |
| EP | 1 416 019 A1 | 5/2004 |
| EP | 1 640 389 A1 | 3/2006 |
| WO | 98/01478 | 1/1998 |
| WO | 98/58974 | 12/1998 |
| WO | 99/31144 | 6/1999 |
| WO | 00/40630 | 7/2000 |
| WO | 01/44389 | 6/2001 |
| WO | 03/046020 | 6/2003 |
| WO | 03/106010 | 12/2003 |
| WO | WO 2007/124803 | * 11/2007 |

* cited by examiner

*Primary Examiner* — David W Wu
*Assistant Examiner* — Robert Jones, Jr.
(74) *Attorney, Agent, or Firm* — Norris McLaughlin & Marcus PA

(57) ABSTRACT

Low-VOC mixture of at least partially salified copolymers of at least one ethylenically unsaturated, phenyl-group-containing monomer and at least one α,β-unsaturated monocarboxylic acid and/or at least one α,β-unsaturated dicarboxylic acid, of at least one water-soluble polyether, esterification products of at least one water-soluble polyether and an aliphatic dicarboxylic acid, and of a star polymer obtainable by esterifying a carboxylic acid containing at least 3 carboxyl groups with at least one water-soluble polyether, and use thereof as a wetting and dispersing agent, preferably for producing low-VOC pigment pastes or low-VOC paint systems.

31 Claims, No Drawings

WETTING AND DISPERSING AGENT

This application is a Continuation of PCT/EP2009/000699, filed Feb. 3, 2009, which claims priority to German application 10 2008 007 713.5, filed Feb. 4, 2008.

The present invention relates to mixtures with a low in volatile organic compounds (VOC) content and composed of at least partially salified copolymers of at least one ethylenically unsaturated, phenyl-group-containing monomer and at least one α,β-unsaturated monocarboxylic acid and/or at least one α,β-unsaturated dicarboxylic acid, of at least one water-soluble polyether, esterification products of at least one water-soluble polyether and an aliphatic dicarboxylic acid, and of a star polymer obtainable by esterifying a carboxylic acid containing at least 3 carboxyl groups with at least one water-soluble polyether, and also to the use of a mixture of the invention as a wetting and dispersing agent, preferably for producing low-VOC pigment pastes or low-VOC paint systems.

In accordance with correspondingly more stringent environmental guidelines, more low-VOC paints are now increasingly being developed. Consequently, among both decorative paints and architectural paints, and also with automobile paints, it is primarily only low-VOC systems which are used for coating, or painting, where the fraction of volatile organic solvents (VOC=volatile organic compounds) must not exceed the limits defined according to ISO 11890-2 or DIN 55649.

Only when the levels of volatile organic solvents are below these limits defined in the stated ISO and DIN standards can such systems be classed as low-VOC. Consequently, there continues to be an urgent need for wetting and dispersing agents suitable for dispersing any of a very wide variety of pigments in such a way that aqueous, low-VOC pigment concentrates produced from them ensure the necessary stability in storage and the necessary rheological properties both in pigment pastes and in corresponding paint systems. This demand exists in respect of the use both of organic and of inorganic pigments.

Many known wetting and dispersing agents, however, are not so universally useful, since they ensure the preparation only of aqueous dispersions of a particular kind of pigment.

Thus U.S. Pat. No. 4,243,430 describes the use of a combination of copolymers containing carboxyl groups, prepared from ethylenically unsaturated monomers and present in the form of ammonium and zinc salts, and nonionic or anionic, polyether-containing wetting agents such as, for example, ethoxylated fatty acids, as wetting and dispersing agent. The use of zinc ions and zinc complexes in wetting and dispersing agents is unacceptable on environmental grounds.

U.S. Pat. No. 6,242,499 discloses the use of partial esters of polyfunctional carboxylic acids with polyglycidols as wetting and dispersing agents for nanoscale solids in cosmetic preparations.

As wetting and dispersing agents for inks, U.S. Pat. No. 6,683,121 recommends a combination of carboxyl-containing copolymers, synthesized from ethylenically unsaturated monomers, and block copolymers which are synthesized from ethylene oxide and propylene oxide and have an HLB of between 16 and 32.

In the light of this prior art, the object was to provide a low-VOC wetting and dispersing agent enabling the preparation of aqueous concentrates both of organic and of inorganic pigments, exhibiting excellent stability in storage and very good rheological properties, hence making them readily suitable for further processing in aqueous coating materials or universal tinting paste systems.

This object is achieved by the provision of the wetting and dispersing agents of the invention, comprising a low-VOC mixture composed of I 10% to 80% by weight of an at least 50% salified copolymer comprising polymerized units of at least one ethylenically unsaturated, phenyl-group-containing monomer and at least one preferably aliphatic, α,β-unsaturated monocarboxylic acid and/or at least one preferably aliphatic, α,β-unsaturated dicarboxylic acid, and optionally derivatives thereof, II 1% to 30% by weight of at least one water-soluble, linear, preferably aliphatic polyether which contains a terminal OH end group and is synthesized to an extent of at least 25 mol % from ethylene oxide units, III 5% to 80% by weight of at least one esterification product of an aliphatic dicarboxylic acid, which preferably has a number-average molecular weight of 400 g/mol to 1000 g/mol, and of at least one water-soluble polyether of component II having preferably a number-average molecular weight of $\leq$2000 g/mol or of a mixture of polyethers which comprises at least one water-soluble polyether of component II having preferably a number-average molecular weight of $\leq$2000 g/mol, and IV 3% to 80% by weight of at least one star polymer obtainable by esterifying at least one aliphatic carboxylic acid containing three to five carboxyl groups, and preferably having a molecular weight of 500 g/mol to 1500 g/mol, with at least one of the water-soluble polyethers of component II having preferably a number-average molecular weight of $\leq$2000 g/mol, or with a mixture of polyethers containing at least one water-soluble polyether of component II having preferably a number-average molecular weight of $\leq$2000 g/mol, the % by weight of components I-IV being based in each case on the total weight of components I-IV, and it being necessary for the sum of the % by weight of components I to IV always to be 100% by weight.

The low-VOC mixture of the invention preferably comprises

30% to 70% by weight of component I,
2% to 10% by weight of component II,
10% to 50% by weight of component III,
and
5% to 20% by weight of component IV, it being necessary for the sum of the % by weight of components I to IV always to be 100% by weight, and the % by weight of components I-IV being based in each case on the total weight of components I-IV.

Component I of the mixture comprises an at least 50%, preferably at least 75%, salified, linear copolymer which has been prepared by polymerizing at least one ethylenically unsaturated monomer preferably having 8-20 C atoms, substituted by at least one phenyl group, and at least one α,β-unsaturated, preferably aliphatic, monocarboxylic acid having preferably 3-8 C atoms, and/or from at least one α,β-unsaturated, preferably aliphatic, dicarboxylic acid having preferably 4-10 C atoms and/or cyclic anhydrides thereof, and optionally respective derivatives thereof, such as esters and amides. The number-average molecular weight of these copolymers is 1000 g/mol to 20 000 g/mol, preferably 1500 g/mol to 10 000 g/mol.

As preferably aliphatic, α,β-unsaturated monocarboxylic or dicarboxylic acid it is preferred to use monocarboxylic acids having 3 to 8 carbon atoms, more preferably acrylic acid and/or methacrylic acid, and/or α,β-unsaturated dicarboxylic acid having 4 to 10 carbon atoms and/or cyclic anhydrides thereof, more preferably maleic acid, fumaric acid, itaconic acid and/or maleic anhydride, and optionally respective derivatives thereof, more preferably their esters, amides, very preferably $C_1$ to $C_6$ alkyl acrylates and/or $C_1$ to $C_6$ alkyl methacrylates.

As phenyl-group-containing, ethylenically unsaturated monomers it is preferred to use monoethylenically unsaturated monomers having 8 to 20 C atoms, more preferably styrene, aryl (meth)acrylates such as benzyl (meth)acrylate, phenyl acrylate, it being possible for the phenyl radicals to be substituted optionally 1 to 4 times, such as 4-methylphenyl (meth)acrylate, for example. Very particular preference is given to using optionally substituted styrene.

The copolymers of component I may be synthesized preferably from 10% to 90% by weight of phenyl-group-containing, ethylenically unsaturated monomers and 90% to 10% by weight of α,β-unsaturated monocarboxylic and/or dicarboxylic acids.

The copolymers of component I may possess a random, alternating, gradient or block construction. Copolymers with a gradient construction are described in, for example, EP-1416019 and also in WO 01/44389. A block construction, such as an AB, ABC or ABA block construction, for example, can be acquired by the copolymers of component I in accordance with disclosure in WO 00/40630, WO 03/046020, U.S. Pat. No. 5,085,698, U.S. Pat. No. 5,160,372, U.S. Pat. No. 5,519,085, U.S. Pat. No. 6,849,679 or US 2007/0185272.

Especially preferred copolymers of component I are styrene/maleic anhydride copolymers (SMA resins) having a styrene-to-maleic anhydride ratio of 1:1 to 8:1. 1:1 to 2:1 is particularly preferred. Their number-average molecular weight corresponds to the figures above.

The copolymers of component I may be prepared via free-radially initiated polymerizations such as with azo or peroxide initiators, for example. In order to set the desired molecular weight, it is possible to add chain regulators such as, for example, thiols, secondary alcohols or alkyl halides such as carbon tetrachloride during the polymerization. Other preparation processes which can be used for the copolymers, preferably SMA resins, include controlled, free-radical polymerization processes, such as, for example the Reversible Addition Fragmentation Chain Transfer Process (RAFT), which when certain polymerization regulators are used is also called MADIX and Addition Fragmentation Chain Transfer, and is identified in the present context as RAFT, as is described in, for example, Polym. Int. 2000, 49. 993. Aust. J. Chem. 2005, 58, 379, J. Polym. Sci. Part A: Polym. Chem. 2005, 43, 5347, U.S. Pat. No. 6,291,620, WO 98/01478, WO 98/58974, and WO 99/31144;

controlled polymerization with nitroxyl compounds as polymerization regulators (NMP), as disclosed in, for example, Chem. Rev. 2001, 101, 3661.

These disclosures in the stated references are hereby incorporated as part of the disclosure of the present specification.

The copolymers of component I are preferably at least 50%, more preferably at least 75%, salified in order that the copolymer acquires solubility in water. For low-VOC salification of the copolymers it is preferred to use alkali metal or alkaline earth metal compounds, preferably corresponding hydroxides, hydrogen carbonates or carbonates. Especially preferred is the use of an alkali metal compound, such as a corresponding hydroxide, hydrogen carbonate or carbonate. Especially preferred more particularly for salification is the use of sodium or potassium hydroxide, sodium or potassium hydrogen carbonate or sodium or potassium carbonate.

It is also possible, moreover, to achieve salification of the copolymers especially those copolymers with maleic anhydride moieties, by amidating the maleic acid with low-VOC N,N-disubstituted diamines, with formation of amides of the maleic acid unit and of a zwitterionic structure as a result of internal salification of the carboxyl groups formed in the course of the amidation.

Particularly suitable for this kind of salification are N,N-substituted diamines of the general formula $R_2N-R'-NH_2$, in which R is an aliphatic, cycloaliphatic, aromatic or aliphatic-aromatic hydrocarbon radical, preferably an alkyl radical with $C_1$ to $C_{10}$, a cycloalkyl radical with $C_4$ to $C_8$, an arylalkylene radical with $C_7$ to $C_{10}$ or an aryl radical with $C_6$ to $C_{12}$. The radical R is preferably a methyl, ethyl, propyl, 2-ethylhexyl, cyclohexyl, benzyl or phenyl radical, with methyl and ethyl radicals being particularly preferred. In the general formula above, the radical R' is an aliphatic, cycloaliphatic, aromatic or aliphatic-aromatic hydrocarbon radical having 2 to 20 carbon atoms. Particularly preferred N,N-substituted diamines used are N,N-dialkylaminoalkylamines, very preferably N,N-dimethylaminoethylamine, N,N-dimethylaminopropyl-amine, N,N-diethylaminoethylamine or N,N-diethylamino-propylamine.

It is also possible to use tertiary, low-VOC amines for salifying the carboxyl groups of the copolymers of component I. Examples of such tertiary amines are alkoxylated amines, of the kind described in, for example, US 2006/0089426, and among which bis[ω-hydropoly-[oxyethylene]oleylamine] can be cited as a representative compound.

As component II of the mixture of the invention it is preferred to use a known polyether synthesized to an extent of at least 25 mol % from ethylene oxide, preferably from at least 50 mol % of ethylene oxide units.

Polyethers of this kind are prepared starting preferably with $C_1$ to $C_4$ monoalcohols, and contain a hydroxyl group as end group.

Component II comprises at least one water-soluble polyether synthesized to an extent of at least 25 mol %, preferably at least 50 mol %, of ethylene oxide units.

Besides the ethylene oxide units of the polyethers employed in accordance with the invention, and optionally other alkylene oxide units, the polyethers may also be based on styrene oxide units and glycidyl ether units.

Besides the ethylene oxide units, the water-soluble polyether used as component II may have other alkylene oxide units having 3 to 10 C atoms, preferably propylene oxide and/or butylene oxide units. Furthermore, it is also possible for there to be, in addition to the ethylene oxide units, units of styrene oxide, and also aliphatic or aromatic glycidyl ethers having 3 to 20 C atoms, preferably isopropyl glycidyl ether, n-butyl glycidyl ether, phenyl glycidyl ether and/or 2-ethylhexyl glycidyl ether, as units of the polyether employed.

In addition, the polyethers may also have been chain-extended with ester units which derive more particularly from aliphatic lactones having 3 to 10 C atoms, preferably from propiolactone, valerolactone and/or ε-caprolactone.

The number-average molecular weight of the polyethers employed in accordance with the invention is preferably from 100 g/mol to 2000 g/ml.

Component III is preferably at least one triblock copolymer which has been obtained by esterification of an aliphatic dicarboxylic acid with a water-soluble polyether or of a mixture of polyethers which comprises at least one water-soluble polyether. The water-soluble polyether, or at least one water-soluble polyether of the mixture of polyethers, corresponds preferably to component (II).

The aliphatic dicarboxylic acid preferably possesses a molecular weight of 400 g/mol to 1000 g/mol.

As aliphatic, saturated or unsaturated dicarboxylic acid it is possible with preference to use the following:

a dimerized fatty acid, which optionally may have been hydrogenated. It is also known to the skilled worker as dimer acid. These dimer acids may be obtained preferably by oligomerization of unsaturated fatty acids having 12 to 22 C atoms, preferably by oligomerization of oleic acid, linolenic acid and/or erucic acid. Dimerized fatty acids, i.e., dimer acids, having a carbon chain of up to 36 C atoms are preferred;

a reaction product of cyclic, aliphatic, optionally unsaturated dicarboxylic acid anhydrides with aliphatic diols or diamines, preferably in a ratio of 2:1. In this context it is possible with preference to use the cyclic dicarboxylic anhydrides such as maleic anhydride or succinic anhydride.

The diols employed for this purpose are preferably aliphatic, linear, cyclic or branched diols having 2 to 20 C atoms. Examples of such diols are ethylene glycol, 1,2-propanediol, 1,3-propanediol, 1,4-butanediol, 1,2-pentanediol, and 1,6-hexanediol.

Furthermore, the diols may also be chain-extended as a result of reaction with aliphatic lactones by formation of oligoesters or polyesters. These dihydroxy-terminated polyesters may be obtained preferably by polymerization of one or more optionally alkyl-substituted lactones having 3 to 10 C atoms, such as propiolactone, valerolactone or caprolactone, for example, using the above-described diols as starter components, in accordance with details in EP-A-154 678 (U.S. Pat. No. 4,647,647).

The diamines which are reacted may preferably be aliphatic, linear, cyclic or branched diamines having 2 to 20 C atoms and two primary amino groups. Examples of such diamines are ethylenediamine, 1,2-propanediamine, 1,3-propanediamine, 1,6-hexanediamine, isophoronediamine, and 3,3'-dimethyl-4,4'-diaminodicyclo-hexylmethane.

Component (IV) is a star polymer which has been obtained by esterification of at least one aliphatic multicarboxylic acid, having three up to five COOH groups, with a water-soluble polyether or with a mixture of polyethers which comprises at least one water-soluble polyether. The water-soluble polyether, or at least one water-soluble polyether of the mixture of polyethers, corresponds preferably to component (II).

Aliphatic multicarboxylic acids of this kind that are employed preferably have a molecular weight of 500 g/mol to 1500 g/mol. Where a mixture of multi-carboxylic acids is used, the number-average molecular weight is likewise from 500 g/mol to 1500 g/mol.

As aliphatic, multicarboxylic acid having three to five carboxyl groups it is preferred to use the following:

a trimerized fatty acid, which optionally may have been hydrogenated. It is also known to the skilled worker as trimer acid. Trimerized fatty acids having up to 54 C atoms are preferred.

A reaction product of cyclic, aliphatic, optionally unsaturated dicarboxylic anhydrides with aliphatic polyols having 3 to 5 OH groups or polyamines having a total of 3 to 5 primary and secondary amino groups, in a stoichiometric ratio of one amino function to one anhydride function. Cyclic carboxylic anhydrides which can be used in this context include, preferably, maleic anhydride or succinic anhydride.

As polyols it is possible to use aliphatic, linear, cyclic or branched polyols having 3 to 20 C atoms and 3 to 5 OH groups, such as glycerol, for example.

Furthermore, the polyols may also be chain-extended as a result of reaction with lactones through formation of oligoesters or polyesters. Polyesters of this kind, terminated with 3 to 5 OH groups, can be obtained by polymerization of one or more, optionally alkyl-substituted lactones having 3 to 10 C atoms, such as propiolactone, valerolactone or caprolactone, for example, using the above-described polyols as starter components, and in accordance with the details in EP-A-154 678 (U.S. Pat. No. 4,647,647).

The polyamines employed for the reaction may preferably be aliphatic, linear, cyclic or branched polyamines having 3 to 20 C atoms and having a total of 3 to 5 primary and secondary amino groups, such as dipropylenetriamine, for example.

In the esterification reaction for preparing components (III) and (IV) it is possible for the dicarboxylic acid and the multicarboxylic acid to be esterified separately in each case. Alternatively they can be used as a mixture for the esterification.

For the esterification it is preferred as dicarboxylic and multicarboxylic acid to use a dimer acid and a trimer acid, which, according to manufacturer and degree of purity, may be obtainable commercially in the form of a mixture of monomeric fatty acid, dimer acid, and trimer acid, with different proportions. The trimer acid in particular may also include small fractions of oligomers which have more than three carboxylic acid functions. The dimer acids listed below typically contain <8% by weight of monomeric fatty acids and up to 25% of trimer acids.

Commercial dimer acid products are Empol® 1008, Empol® 1061, Empol® 1062, Pripol® 1006, Pripol® 1007, and Pripol® 1022.

Commercial trimer acid products are Empol® 1041 and Pripol® 1040.

It is especially preferred as dicarboxylic acids and/or multicarboxylic acids to use the dimer and trimer acids listed in order to prepare the components (III) and (IV).

The esterification of the dicarboxylic and multicarboxylic acids with the polyethers, preferably of component (II), is carried out by methods known to the skilled worker. Hence the reaction of the mixture may be carried out in the presence of an esterification catalyst, which is, for example, a sulfonic acid, dibutyltin dilaurate or a tertiary amine, at reaction temperatures up to 300° C., preferably up to 200° C. The water liberated in the course of the esterification may be removed either azeotropically with a suitable entrainer such as xylene, benzene or carbon tetrachloride, for example, or by application of vacuum.

The esterification is taken preferably to a degree of conversion of at least 90% of the acid functions of the dicarboxylic acids and multicarboxylic acids.

In the course of the esterification it is also possible with preference to use an excess of polyether, which forms component (II) in the mixture of the invention.

In the mixture of the invention there may also, however, be a further polyether, as component II, which is different from the polyethers used in the esterification.

The triblock copolymer of component (III) and the star polymer of component (IV) have a water-insoluble segment having a number-average molecular weight of 400 g/mol to 1000 g/mol for component III and of 500 g/mol to 1500 g/mol for component IV, thereby allowing the pigments to be stabilized more effectively in an aqueous dispersion. If this segment is too short or too water-soluble, then a pigment dispersion is no longer sufficiently stable, and the pigments flocculate. If the water-insoluble segment is too long, the components (III) and (IV) form micelles in water. Generally speaking, micelles display poorer dispersing behavior than the corresponding unimers, and so formation of micelles is undesirable.

The mixtures of the invention are suitable as wetting and dispersing agents for many water-based applications known from the prior art. For instance, they may be used, for example, in connection with the production or processing of paints, printing inks, inks for inkjet processes such as for inkjet printers, paper coating, leather colorants and textile colorants, pastes, pigment concentrates, ceramics, cosmetic preparations, preferably whenever solids such as pigments and/or fillers are present. By way of example, the mixtures of the invention may be used in association with the production of industrial coatings, wood and furniture coatings, vehicle coatings, marine paints, anticorrosion paints, can coatings and coil coatings, decorative paints, and architectural paints, and for these purposes, if desired, conventional, known binders and/or low-VOC solvents, pigments, and optionally fillers, the polymer mixtures of the invention, and conventional auxiliaries are mixed.

Examples of conventional binders are resins based on polyurethanes, cellulose nitrates, cellulose acetobutyrates, alkyds, melamine, polyesters, chlorinated rubber, epoxies, and acrylates.

As wetting and dispersing agents, the low-VOC mixtures of the invention are also suitable for producing water-based coatings, such as cathodic or anodic electro-deposition coatings, for automobile bodies, for example. Other examples of the dispersing agent utility are in renders, silicate paints, emulsion paints, aqueous paints based on water-dilutable alkyds, alkyd emulsions, hybrid systems, 2-component systems, polyurethane dispersions, and acrylate dispersions.

The mixtures of the invention are also suitable more particularly for producing concentrates of solids, preferably pigment concentrates. For this purpose, they are introduced in water, or in a mixture of water and low-VOC, organic, water-miscible solvents or plasticizers, and the solids to be dispersed are added with stirring. These concentrates may further comprise binders and/or other auxiliaries.

The auxiliaries which may be added to pigment concentrates are, for example
- defoamers, such as mineral-oil defoamers and silicone defoamers;
- rheology control agents, such as polyurethane thickeners, fumed silicas, polyamide compounds, and oligourea compounds;
- flow control agents;
- antioxidants;
- biocides;
- organically modified oligosiloxanes and polysiloxanes for surface wetting.

With the mixtures of the invention it is also possible, however, in an advantageous way to prepare stable, binder-free pigment concentrates. It is likewise possible to use the mixtures of the invention to produce fluid pigment concentrates from pigment filtercakes. In this case, the filtercake, which may still contain water, is admixed with a mixture of the invention, and the resulting mixture is dispersed. Concentrates of solids of this kind, preferably pigment concentrates, may then be incorporated into various substrates such as, for example, alkyd resins, polyester resins, acrylate resins, polyurethane resins or epoxy resins. Pigments which are dispersed directly in the mixtures of the invention without solvent are particularly suitable for pigmenting thermoplastic and thermosetting plastics formulations.

The polymer mixtures of the invention may also be used with advantage in the production of inks for non impact printing processes such as thermal inkjet and the bubblejet process. These inks, for example, may be aqueous ink formulations.

The mixtures of the invention can also be employed in the production of cosmetic preparations, such as for producing make-up, powder, lipsticks, hair colorants, creams, nail varnishes, and sun protection products. These preparations may be present in the typical formulations, such as in the form of W/O or O/W emulsions, solutions, gels, creams, lotions or sprays. The mixtures of the invention may in this case even be used as dispersing agents in the dispersions that are used to produce these preparations.

The present invention further provides, additionally, for the use of the mixtures of the invention as wetting and dispersing agents. These wetting and dispersing agents are preferably employed for the applications described above.

A further application, moreover, is the production of a pigmented coating on a substrate, where the pigmented paint is applied to the substrate, and the pigmented paint applied is baked or cured, or crosslinked.

For the applications of the mixtures of the invention they may be used, if desired, together with binders that are conventional in accordance with the prior art.

One of the uses in accordance with the invention is also in the production of dispersible solids in powder particle and/or fiber particle form, more particularly in the production of dispersible pigments, where the particles may be coated with a mixture of the invention. Coating operations of this kind on organic or inorganic solids are performed in a known way, as described in EP-A-0 270 126, for example. In this case, the low-VOC solution or emulsion medium may either be removed or remain in the mixture, to form a paste. Pastes of this kind are common commercial products, which if desired may comprise binders and also other auxiliaries and adjuvants.

Specifically in the case of pigments, the modification, i.e., coating of the pigment surface, may be accomplished by adding the mixtures of the invention during or after the synthesis of the pigments, i.e., by their addition to the pigment suspension, or during or after the pigment finish.

The pigments pretreated in this way are notable for greater ease of incorporability and for a higher color strength as compared with pigments that have not been surface treated.

The mixtures of the invention are suitable as wetting and dispersing agents for a multiplicity of pigments, such as monoazo, diazo, triazo, and polyazo pigments, oxazine, dioxazine and thiazine pigments, diketopyrrolopyrroles, phthalocyanines, ultramarine, and other metal-complex pigments, indigoid pigments, diphenylmethane, triarylmethane, xanthene, acridine, quinacridone, and methine pigments, anthraquinone, pyranthrone, perylene, and other polycyclic carbonyl pigments. Further examples of organic pigments which can be dispersed in accordance with the invention are found in the following monograph: W. Herbst, K. Hunger, "Industrial Organic Pigments", 1997 (publisher: Wiley-VCH, ISBN: 3-527-28836-8). Examples of inorganic pigments which can be dispersed in accordance with the invention are pigments based on carbon black, graphite, zinc, titanium dioxide, zinc oxide, zinc sulfide, zinc phosphate, barium sulfate, lithopones, iron oxide, ultramarine, manganese phosphate, cobalt aluminate, cobalt stannate, cobalt zincate, antimony oxide, antimony sulfide, chromium oxide, zinc chromate, mixed metal oxides based on nickel, bismuth, vanadium, molybdenum, cadmium, titanium, zinc, manganese, cobalt, iron, chromium, antimony, magnesium, aluminum (for example, nickel titanium yellow, bismuth vanadate molybdate yellow or chromium titanium yellow). Other examples are cited in the following monograph: G. Buxbaum, "Industrial Inorganic Pigments", 1998 (publisher: Wiley-VCH, ISBN: 3-527-28878-3). Inorganic pigments may also be magnetic pigments based on pure iron, iron oxides, and chromium oxides or mixed oxides, metallic-effect pigments comprising aluminum, zinc, copper or brass, and also pearlescent pigments, and fluorescent and phosphorescent pigments.

The polymer mixtures of the invention can also be used to disperse nanoscale organic or inorganic solids having particle sizes of below 100 nm, such as certain types of carbon black, or particles composed of a metal or semimetal oxide or hydroxide, and also particles composed of mixed metal and/or semimetal oxides or hydroxides. Oxides suitable for this purpose are oxides and/or oxide hydroxides of aluminum, of silicon, of zinc, of titanium, which can be used for preparing such extremely finely divided solids. The operation of producing these oxidic and/or hydroxidic and/or oxide-hydroxidic particles may proceed via various methods, examples being ion exchange operations, plasma operations, sol-gel processes, precipitation, comminution (by grinding, for example) or flame hydrolysis, etc. These nanoscale solids may also be what are called hybrid particles, which are constructed from an inorganic core and an organic shell, or vice versa.

Fillers in powder or fiber form that are dispersible in accordance with the invention include those which are constructed from particles, in powder or fiber form, of aluminum oxide, aluminum hydroxide, silicon dioxide, kieselguhr, siliceous earth, quartz, silica gel, talc, kaolin, mica, perlite, feldspar, finely ground slate, calcium sulfate, barium sulfate, calcium carbonate, calcite, dolomite, glass or carbon. Other examples of dispersible pigments or fillers are also to be found in EP-A-0 270 126. Matting agents as well, such as silicas, for example, can likewise be outstandingly dispersed and stabilized with the mixtures of the invention.

The present invention accordingly further provides paints and pastes comprising at least one mixture of the invention and at least one pigment, water, and, if desired, a low-VOC, organic vehicle, and also, if desired, binders and typical auxiliaries.

The present invention therefore also further provides the aforementioned pigments coated with at least one mixture of the invention.

EXAMPLES

I Preparation of the Copolymers with Carboxyl Groups

Polymer 1: Alternating SMA Resin Having a Styrene to MAn Ratio of 2:1

27.3 g of methoxypropyl acetate, 4.2 g of 2,4-diphenyl-4-methyl-1-pentene, and 3.3 g of styrene are heated to 140° C. When the reaction temperature has been reached, 14.4 g of maleic anhydride and 2.3 g of AMBN, partially dissolved in 21.7 g of methoxypropyl acetate, are metered in over 100 min, and 26.8 g of styrene are metered in over 85 min.

After a subsequent reaction time of 1 h, the polymer solution is cooled to room temperature.

Residual 2,4-diphenyl-4-methyl-1-pentene content: 0.1%
$M_n$: 2775 g/mol

Polymer 2: Alternating SMA Resin Having a Styrene to MAn Ratio of 1:1

11.3 g of methoxypropyl acetate and 5.8 g of 2,4-diphenyl-4-methyl-1-pentene are heated to 140° C. When the reaction temperature has been reached, 20.4 g of maleic anhydride and 2.8 g of AMBN, partially dissolved in 38.1 g of methoxypropyl acetate, are metered in over 100 min, and 21.6 g of styrene are metered in over 100 min.

After a subsequent reaction time of 1 h, the polymer solution is cooled to room temperature.

Residual 2,4-diphenyl-4-methyl-1-pentene content: 0.1%
$M_n$: 1886 g/mol

Polymer 3: Diblock Copolymer 27.3 g of methoxypropyl acetate and 4.2 g of 2,4-diphenyl-4-methyl-1-pentene are heated to 140° C. When the reaction temperature has been reached, 14.4 g of maleic anhydride and 2.3 g of AMBN, partially dissolved in 21.7 g of methoxypropyl acetate, are metered in over 100 min, and 26.8 g of styrene are metered in over 85 min. After a subsequent reaction time of 15 min, 1 g of AMBN, partially dissolved in 10 g of methoxypropyl acetate, and 10 g of styrene are metered in over 100 min.

After a subsequent reaction time of 1 h, the polymer solution is cooled to room temperature.

Residual 2,4-diphenyl-4-methyl-1-pentene content: 0.08%
$M_n$: 3156 g/mol

Polymer 4: Diblock Copolymer 22.8 g of methoxypropyl acetate, 13.8 g of BlocBuilder, and 31.2 g of styrene are heated to 120° C. When the reaction temperature has been reached, 24.7 g of acrylic acid, partially dissolved in 7.6 g of methoxypropyl acetate, are metered in over 100 min. After a subsequent reaction time of 2 h, the polymer solution is cooled to room temperature.

$M_n$: 2835 g/mol

The molecular weights were measured by means of gel permeation chromatography, using THF as eluent and polystyrene as standard.

II Salified Copolymers

Polymer Solution 1

100 g of a solution of polymer 1 in methoxypropyl acetate are admixed with 10.7 g of NaOH and 91.05 g of water and heated to 100° C., the methoxypropyl acetate being distilled off as an azeotrope.

The mixture is diluted with water to a solids of 40% by weight.

Polymer Solution 2

100 g of a solution of polymer 2 in methoxypropyl acetate are admixed with 23.6 g of KOH and 110.4 g of water and heated to 100° C., the methoxypropyl acetate being distilled off as an azeotrope.

The mixture is diluted with water to a solids of 40% by weight.

Polymer Solution 3

100 g of a solution of polymer 2 in methoxypropyl acetate are admixed with 21.4 g of dimethylaminopropyl-amine and 107.1 g of water and heated to 100° C., the methoxypropyl acetate being distilled off as an azeotrope.

The mixture is diluted with water to a solids of 40% by weight.

Polymer Solution 4

12.2 g of KOH are dissolved in 60 g of water and then 27.78 g of SMA 1000 resin are dissolved at 80° C.

Polymer Solution 5

100 g of a solution of polymer 4 in methoxypropyl acetate are admixed with 21.5 g of KOH and 122.3 g of water and heated to 100° C., the methoxypropyl acetate being distilled off as an azeotrope.

The mixture is diluted with water to a solids of 40% by weight.

Polymer Solution 6

16 g of KOH are dissolved in 250 g of water and then 50 g of SMA 1000 resin are dissolved at 80° C. Subsequently 150 g of an alkoxylated tertiary diamine (example 9 from US 2006/0089426) are added.

The mixture is diluted with water to a solids of 40% by weight.

III Esterification Products

Ester 1:

10.04 g of Pripol 1022 are introduced with 29.92 g of Pluriol A 750 E and 0.1 g of para-toluenesulfonic acid and this initial mixture is reacted at 210° C., the water formed being separated off. The reaction is at an end when 90% of the carboxyl groups have been esterified. Subsequently the solids is adjusted with water to 40% by weight.

Ester 2:

24.35 g of Pripol 1022 are introduced with 202.7 g of Pluriol A2300PE and 0.15 g of para-toluenesulfonic acid and this initial mixture is reacted at 210° C., the water formed being separated off. The reaction is at an end when 90% of the carboxyl groups have been esterified. Subsequently the solids is adjusted with water to 40% by weight.

Ester 3 (Comparative Example):

10.04 g of Pripol 1022 are introduced with 14.96 g of Pluriol A 750 E and 0.06 g of para-toluenesulfonic acid and this initial mixture is reacted at 210° C., the water formed being separated off. The reaction is at an end when only 50% of the carboxyl groups have been esterified. Subsequently the solids is adjusted with water to 40% by weight.

Ester 4 (Comparative Example):

8.72 g of tall oil fatty acid are introduced with 26.1 g of Pluriol A 750 E and 0.06 g of para-toluenesulfonic acid and this initial mixture is reacted at 210° C., the water formed being separated off. The reaction is at an end when 90% of the carboxyl groups have been esterified. Subsequently the solids is adjusted with water to 40% by weight.

IV Mixture of Salified Copolymers (Products II) and of Esterification Products (Products III)

Wetting and Dispersing Agent 1 (Inventive) (W&D1)

50 g of polymer solution 4 are mixed with 50 g of ester 1 and homogenized.

Wetting and Dispersing Agent 2 (Comparative Example) (W&D2)

50 g of polymer solution 4 are mixed with 50 g of ester 3 and homogenized.

Wetting and Dispersing Agent 3 (Comparative Example) (W&D3)

50 g of polymer solution 4 are mixed with 50 g of ester 4 and homogenized.

BlocBuilder: Polymerization initiator, manufacturer: Arkema

SMA 1000 resin: Styrene/maleic anhydride copolymer; manufacturer: Cray Valley

Pripol 1022: Dimer acid (1-3% monoacid, 74-85% dimer acid, 15-23% trimer acid); manufacturer: UniQuema Pluriol A750E: Polyether glycol prepared starting from methanol; manufacturer: BASF Pluriol A2300PE: EO-PO polyether prepared starting from 1-butanol; manufacturer: BASF V Application Tests 5.1 Formulations 5.1.1 Aqueous Pigment Concentrates:

|  | Tronox CR 826 | Monarch 120 | Heliogen Blue L7101F |
|---|---|---|---|
| Water | 20.15 | 58.9 | 37.65 |
| W&D 1, 2 or 3 or ester 1 or SMA solution 4 | 3.75 | 20 | 26.25 |
| BYK ®-024 | 1.0 | 1.0 | 1.0 |
| Parmetol A26 | 0.1 | 0.1 | 0.1 |
| Pigment | 75 | 20 | 35.0 |
| % by weight | 100.00 | 100.00 | 100.00 |

W&D = wetting and dispersing agent

The pigment concentrate comprising the Tronox pigment is prepared with a dissolver at 10 m/s stirring speed in a dispersing time of 29 min.

The other two pigments are dispersed for 120 min using a Skandex shaker and glass beads.

5.1.2 Pigmented Paints:

| Clear varnish | |
|---|---|
| Mowilith LDM 7416 | 71.30 |
| Water | 13.30 |
| AMP 90 | 0.20 |
| Propylene glycol | 1.50 |
| Texanol | 2.00 |
| Water | 3.60 |
| BYK-028 | 0.50 |
| Tafigel PUR 40 | 0.30 |
| Parmetol A 26 | 0.20 |
| Dissolver 5 min 3 m/s | |
| BYK-348 | 0.50 |
| Water | 6.60 |
| Total % by weight | 100.00 |

Let-Downs:

Tronox (as Pigment):

| Pigment concentrate | 12 g |
|---|---|
| Clear varnish | 30 g |
|  | 42 g |

Heliogen Blue or Monarch (as Pigment):

| Pigment concentrate | 3 g |
|---|---|
| Clear varnish | 30 g |
|  | 33 g |

The pigment concentrate is shaken with the varnish for 5 min.

Tronox CR 826: titanium dioxide pigment, manufacturer: Tronox

Heliogen Blue L7101F: phthalocyanine pigment, manufacturer: BASF

Monarch 120: carbon black pigment, manufacturer: Cabot

BYK®-024: defoamer, manufacturer: Byk Chemie GmbH

Parmetol A26: preservative, manufacturer: S&M-Chemie

Mowilith LDM7416: styrene/acrylate copolymer dispersion, manufacturer: Celanese

AMP90: 2-amino-2-methylpropanol, manufacturer: Dow

Tafigel PUR 40: associative thickener, manufacturer: Münzing-Chemie

BYK®-028: defoamer, manufacturer: Byk Chemie GmbH

BYK®-348: substrate wetting agent, manufacturer: Byk Chemie GmbH

Texanol: coalescer, manufacturer: Eastman

Propylene Glycol: solvent, manufacturer: Dow 5.2 Test Results 5.2.1 Aqueous Pigment Concentrates

| Pigment | W&D agent | Assessment of pigment concentrates | | |
|---|---|---|---|---|
| | | Viscosity | Particle size | Storage one day, RT |
| Tronox | Ester 1 (comparative) | not dispersible | | — |
| | SMA solution 4 (comparative) | fluid | 15 μm | 1 |
| | W&D 1 | fluid | 15 μm | 1 |
| | W&D 2 (comparative) | fluid | 15 μm | 2 |
| | W&D 3 (comparative) | fluid | 15 μm | 2 |
| Heliogen Blue | Ester 1 | fluid | 15 μm | 1 |
| | SMA solution 4 | highly viscous | 60-100 μm | 3 |
| | W&D 1 | fluid | 15 μm | 1 |
| | W&D 2 | fluid | 25 μm | 1 |
| | W&D 3 | fluid | 10 μm | 1 |
| Monarch | Ester 1 | fluid | 10 μm | 1 |
| | SMA solution 4 | foamy | >100 μm | 2 |
| | W&D 1 | fluid | 10 μm | 1 |
| | W&D 2 | fluid | 10 μm | 1 |
| | W&D 3 | fluid | 10 μm | 1 |

1: No sedimentation of pigments, zero to slight rise in viscosity
2: Sedimentation of pigments
3: No sedimentation of pigments, sharp rise in viscosity The particle size was measured with a 100 μm grindometer in the wet paint, since the aqueous pigment concentrates cannot be applied to the grindometer as a continuous film, because of wetting defects.

5.2.2 Let-Downs

| Pigment | W&D agent | Gloss (20° C.) | Gloss (60° C.) | Bits |
|---|---|---|---|---|
| Tronox | Ester 1 | let-down not possible | | |
| | SMA solution 4 | 19.7 | 52.2 | none |
| | W&D 1 | 15.8 | 55.8 | none |
| | W&D 2 | 13.4 | 54.7 | none |
| | W&D 3 | 18.4 | 58.7 | none |
| Heliogen Blue | Ester 1 | 66.1 | 80 | none |
| | SMA solution 4 | 58.3 | 77.5 | many |
| | W&D 1 | 69.9 | 81.6 | none |
| | W&D 2 | 65.3 | 79.4 | none |
| | W&D 3 | 67.3 | 80.0 | none |
| Monarch | Ester 1 | 65.7 | 80.6 | none |
| | SMA solution 4 | 12.0 | 42.6 | many |
| | W&D 1 | 66.5 | 81.4 | none |
| | W&D 2 | 65.3 | 80.7 | none |
| | W&D 3 | 65.1 | 80.6 | none |

The gloss measurements were made using a color guide sphere from BYK-Gardner.

The results show that not all selected pigments give pigment concentrates and let-downs with sufficient quality using the individual components of the mixture—the nonionic, polyether-containing components (ester 1), on the one hand, and the salified copolymer (SMA solution 4), on the other. A pigment concentrate cannot be produced with ester 1 and the inorganic pigment Tronox.

The salified acidic copolymer is suitable for the inorganic pigment Tronox, but shows weaknesses when the two organic pigments are used (highly viscous or foamy pigment concentrate, in which the pigments are in part still present in the form of agglomerates, and let-downs containing bits).

With the mixture of the invention (wetting and dispersing agent 1) it is possible to prepare fluid and storage-stable pigment concentrates, suitable for the formulation of bit-free paints, from both the inorganic pigment and the two organic pigments.

The Tronox pigment concentrates which comprise the comparative examples, wetting and dispersing agents 2 and 3, exhibit poorer stability in storage than the mixture of the invention.

The invention claimed is:

1. A mixture with a low content of volatile organic compounds (VOC), comprised of the following components:

I 10% to 80% by weight of an at least 50% salified copolymer of at least one ethylenically unsaturated, phenyl-group-containing monomer and at least one α,β-unsaturated monocarboxylic acid and/or at least one α,β-unsaturated dicarboxylic acid, and optionally derivatives thereof, II 1% to 30% by weight of at least one water-soluble, linear polyether which contains a terminal OH end group and is synthesized to an extent of at least 25 mol % from ethylene oxide, III 5% to 80% by weight of at least one esterification product of an aliphatic dicarboxylic acid and of at least one of the water-soluble polyethers of component II having a number-average molecular weight of ≦2000 g/mol or of a mixture of polyethers which comprises at least one water-soluble polyether of component II having a number-average molecular weight of ≦2000 g/mol, and IV 3% to 80% by weight of at least one star polymer obtained by esterifying at least one aliphatic carboxylic acid containing three to five carboxyl groups with at least one of the water-soluble polyethers of component II having a number-average molecular weight of ≦2000 g/mol, or with a mixture of polyethers containing at least one water-soluble polyether of component II having a number-average molecular weight of ≦2000 g/mol, the sum of the % by weight of components I to IV being 100% by weight, and the % by weight of each of components I-IV being based in on the total weight of components I-IV.

2. A mixture according to claim 1, comprising
30% to 70% by weight of component I,
2% to 10% by weight of component II,
10% to 50% by weight of component III, and
5% to 20% by weight of component IV,
the sum of the % by weight of components I to IV being 100% by weight, and the % by weight of each of components I to IV being based on the total weight of components I to IV.

3. A mixture according to claim 1 wherein component I is at least 75% salified.

4. A mixture according to claim 1, wherein component I is in the form of an alkali metal, alkaline earth metal or ammonium salt.

5. A mixture according to claim 1, wherein the salified copolymer of component I is prepared by polymerizing at least one ethylenically unsaturated, phenyl-group-containing monomer having 8 to 20 C atoms, the phenyl radicals optionally being substituted at least once, and at least one α,β-unsaturated monocarboxylic acid having 3 to 8 carbon atoms and/or at least one α,β-unsaturated dicarboxylic acid having 4 to 10 carbon atoms and/or the cyclic anhydrides thereof, and optionally the respective derivatives thereof.

6. A mixture according to claim 5, wherein said ethylenically unsaturated, phenyl-group-containing monomer is selected from the group consisting of styrene, benzyl (meth) acrylate, and phenyl acrylate, the phenyl radicals optionally being substituted 1 to 4 times.

7. A mixture according to claim 5 wherein said α,β-unsaturated monocarboxylic acid is acrylic acid or methacrylic acid, and said α,β-unsaturated dicarboxylic acid and/or cyclic anhydride is at least one dicarboxylic acid selected from the group consisting of maleic acid, fumaric acid, and itaconic acid and/or maleic anhydride, and optionally, as respective derivative thereof, their esters, amides.

8. A mixture according to claim 1, wherein component I is a salified styrene/maleic anhydride copolymer having a styrene to maleic anhydride ratio of 1:1 to 8:1.

9. A mixture according to claim 1, wherein component II is at least one water-soluble polyether synthesized to an extent of at least 50 mol % from ethylene oxide.

10. A mixture as according to claim 1, wherein component II is at least one water-soluble polyether synthesized from units of ethylene oxide and from units of at least one other alkylene oxide.

11. A mixture according to claim 1, wherein component II is at least one water-soluble polyether synthesized from ethylene oxide units and from units of at least one aliphatic or aromatic glycidyl ether having 3 to 20 C atoms, and/or from units of at least one aliphatic lactone having 3 to 10 C atoms.

12. A mixture according to claim 1, wherein component III is the esterification product of at least one water-soluble polyether of component II or of a mixture of polyethers which comprises at least one water-soluble polyether of component II and of an aliphatic, optionally saturated dimer acid which obtained by oligomerizing unsaturated fatty acids having 12 to 22 C atoms.

13. A mixture according to claim 1, wherein component III is the esterification product of at least one water-soluble polyether of component II or of a mixture of polyethers which comprises at least one water-soluble polyether of component II and of an optionally partially esterified, aliphatic dicarboxylic acid obtained by reacting an optionally unsaturated, aliphatic dicarboxylic anhydride, with at least one aliphatic diol with $C_2$ to $C_{20}$, which may optionally be chain-extended as a result of reaction with a dihydroxy-terminated, aliphatic polyester based on at least one aliphatic lactone having 3 to 10 C atoms.

14. A mixture according to claim 1, wherein component III is the esterification product of at least one water-soluble polyether of component II or of a mixture of polyethers which comprises at least one water-soluble polyether of component II and of an optionally partially amidated, aliphatic dicarboxylic acid obtained by reacting an optionally unsaturated, aliphatic dicarboxylic anhydride with at least one linear or branched, aliphatic or cycloaliphatic diamine containing two primary amino groups and having 2 to 20 C atoms.

15. A mixture according to claim 1, wherein component IV is the esterification product of at least one of the water-soluble polyethers of component II or of a mixture of polyethers which comprises at least one water-soluble polyether of component II and of an optionally saturated trimer acid obtained by oligomerizing an unsaturated fatty acid having 12 to 22 C atoms.

16. A mixture according to claim 1, wherein component IV is the esterification product of at least one water-soluble polyether of component II or of a mixture of polyethers which comprises at least one water-soluble polyether of component II, and of at least one aliphatic, optionally partially esterified multicarboxylic acid which contains 3 to 5 carboxyl groups and is obtained by reacting an optionally unsaturated, aliphatic dicarboxylic anhydride with at least one aliphatic polyol having 3 to 5 OH groups, which is optionally chain-extended as a result of reaction with a polyester based on aliphatic lactones having 3 to 10 C atoms, in a stoichiometric ratio of the anhydride function to the hydroxyl function of 1:1.

17. A mixture according to claim 1, wherein component IV is the esterification product of at least one water-soluble polyether of component II or of a mixture of polyethers which comprises at least one water-soluble polyether of component II, and of at least one aliphatic, optionally amidated multicarboxylic acid which contains 3 to 5 carboxyl groups and is obtained by reacting an optionally unsaturated, aliphatic dicarboxylic anhydride with aliphatic polyamines having a total of 3 to 5 primary and/or secondary amino groups, in a stoichiometric ratio of the anhydride function to the amino function of 1:1.

18. A mixture according to claim 1, wherein components III and IV are each an esterification product of a mixture of dimer acid and trimer acid, which is obtained by oligomerizing unsaturated fatty acids having 12 to 22 C atoms, with at least one of the water-soluble polyethers of component II or with a mixture of polyethers which comprises at least one water-soluble ether of component II.

19. A mixture according to claim 18, wherein the ratio of dimer acid to trimer acid in the mixture of dimer acid and trimer acid used is 10:90 to 90:10.

20. A mixture according to claim 19, wherein the dimer acid has up to 36 C atoms and the trimer acid has up to 54 C atoms.

21. A low-VOC wetting and dispersing agent comprising the mixture of claim 1.

22. A method for dispersing solids which comprises dispersing said solids with the wetting and dispersing agent of claim 21.

23. A method for dispersing pigments which comprises dispersing said pigments with the wetting and dispersing agent of claim 21.

24. The method of claim 23 for preparing a low-VOC, aqueous pigment concentrate.

25. A method for producing paints, which comprises producing said paints with an aqueous pigment concentrate produced according to claim 24.

26. An aqueous, low-VOC pigment concentrate comprising the mixture of claim 1 as wetting and dispersing agent.

27. A paint or a paste comprising at least one pigment, a mixture of claim 1, an aqueous dispersion medium, and optionally a low-VOC, organic vehicle, and optionally other auxiliaries.

28. A dispersible, multiparticulate and/or fibrous solid, coated with the mixture of claim 1.

29. The dispersible, multiparticulate solid of claim 28, wherein said multi-particulate solid is a pigment.

30. A method for producing an aqueous ink for the nonimpact printing process, which comprises producing said aqueous ink with the mixture of claim 1.

31. Wetting and dispersing agent for cosmetic preparations, comprising the mixture of claim 1.

* * * * *